(12) United States Patent
Zell et al.

(10) Patent No.: US 11,897,853 B2
(45) Date of Patent: Feb. 13, 2024

(54) SYNTHESIS OF 1,1,2-TRIFLUORO-4-(SUBSTITUTED SUFONYL)-BUT-1-ENE

(71) Applicant: ADAMA MAKHTESHIM LTD., Beer-Sheva (IL)

(72) Inventors: Thomas Zell, Beer-Sheva (IL); Shlomi Cohen, Beer-Sheva (IL)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 62 days.

(21) Appl. No.: 17/419,417

(22) PCT Filed: Dec. 30, 2019

(86) PCT No.: PCT/IL2019/051434
§ 371 (c)(1),
(2) Date: Jun. 29, 2021

(87) PCT Pub. No.: WO2020/141514
PCT Pub. Date: Jul. 9, 2020

(65) Prior Publication Data
US 2021/0387955 A1 Dec. 16, 2021

Related U.S. Application Data

(60) Provisional application No. 62/786,587, filed on Dec. 31, 2018.

(51) Int. Cl.
*C07D 277/36* (2006.01)
*B01J 23/30* (2006.01)

(52) U.S. Cl.
CPC ............ *C07D 277/36* (2013.01); *B01J 23/30* (2013.01)

(58) Field of Classification Search
CPC .................................................... C07D 277/36
See application file for complete search history.

(56) References Cited

U.S. PATENT DOCUMENTS 6,734,198 B1    5/2004   Watanabe et al.

FOREIGN PATENT DOCUMENTS

| JP | 2005507431 A | 3/2005 |
| JP | 2005537249 A | 12/2005 |
| WO | 01/02378 A1 | 1/2001 |
| WO | 2004/005268 A1 | 1/2004 |
| WO | 2006/123088 A2 | 11/2006 |
| WO | 2010143661 A1 | 12/2010 |

OTHER PUBLICATIONS

Li, et al. European Journal of Medicinal Chemistry 93 (2015) 423-430.*
Tony Hargreaves. Catalysts for a green industry. Jun. 30, 2009, 1-10 URL: https://edu.rsc.org/feature/catalysts-for-a-green-industry/2020110.article.*
Muller, et al. "Enantioselective Intramolecular [2 +2]-Photocycloaddition Reactions of 4-Substituted Quinolones Catalyzed by a Chiral Sensitizer with a Hydrogen-Bonding Motif," Journal of the American Chemical Society, 2011, 133(41), pp. 16689-16697, S9.
Sato, et al.. "Oxidation of sulfides to sulfoxides and sulfones with 30% hydrogen peroxide under organic solvent-and halogen-free conditions," Tetrahedron, 2001, 57(13), pp. 2469-2476.

* cited by examiner

*Primary Examiner* — Shawquia Jackson
(74) *Attorney, Agent, or Firm* — Nath, Goldberg & Meyer; Joshua B. Goldberg

(57) ABSTRACT

The present invention provides a process for preparing a compound of formula [I] from a compound of formula [II] using an oxidizing agent and a catalyst, the process is carried out at a low temperature.

34 Claims, 3 Drawing Sheets

SYNTHESIS OF 1,1,2-TRIFLUORO-4-(SUBSTITUTED SUFONYL)-BUT-1-ENE

Throughout this application various publications are referenced. The disclosures of these documents in their entireties are hereby incorporated by reference into this application in order to more fully describe the state of the art to which this invention pertains.

TECHNICAL FIELD

The present subject matter relates to a process for preparing a compound of formula [I]

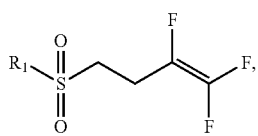

wherein $R_1$ is optionally substituted heterocyclic aromatic ring.

BACKGROUND OF THE INVENTION

Fluensulfone (5-chloro-2-(3,4,4-trifluorobut-3-enylsulfonyl)-1,3-thiazole; CAS No. 318290-98-1) is a very efficient active ingredient highly powerful against plant-parasitic nematodes. Fluensulfone is a heterocyclic fluoroalkenyl sulfone nematicide which has a significantly reduced environmental impact with low toxicity to non-target insects and mammals. Fluensulfone's mode of action is distinct from currently available nematicides and therefore presents a promising entity for crop protection although the precise mode of action of fluensulfone is currently unknown.

Fluensulfone of formula (I), is prepared through oxidation reaction of the compound 5-chloro-2-[(3,4,4-trifluoro-3-buten-1-yl)thio]-thiazole of formula (II). The preparation of formula (II) is described in the international application publication no. WO 01/02378, the contents of which is hereby incorporated by reference.

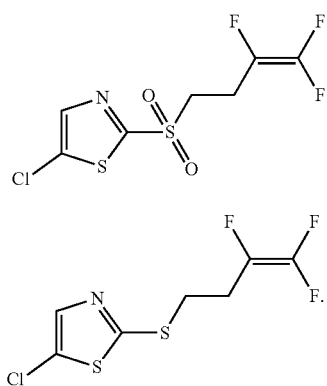

There have been reported processes of preparing fluensulfone by the reaction of the corresponding sulfide with an oxidizing agent.

WO 01/02378 A1 discloses a process for preparing fluensulfone by reacting the corresponding sulfide with hydrogen peroxide in glacial acetic acid at 55-60° C. for 6 h.

U.S. Pat. No. 8,901,311 B2 discloses a process for preparing heterocyclic fluoroalkenyl sulfones and fluoroalkenyl sulfoxides from the corresponding fluoroalkenyl thioethers by the use of oxone. Oxone is expensive and generates a great amount of waste in the form of salts, which is problematic especially in a large scale production.

Processes for preparing other sulfones by a catalytic oxidation of the corresponding sulfides have also been reported.

J. Org. Chem., 28, 1140 (1963) discloses a process of preparing 2-phenylsulfonylethanol by the reaction of 2-phenylmercaptoethanol with hydrogen peroxide in the presence of a sodium tungstate. The disclosed reaction is carried out at 60-75° C.

Tetrahedoron, 57, 2469 (2001) discloses a process using quaternary ammonium hydrogensulfate and phenylphosphonic acid in addition to the sodium tungstate.

EP 0926143 A1 discloses the synthesis of 2-(methylsulfonyl)-5-(trifluoromethyl)-1,3,4-thiadiazole using catalytic oxidation at a temperature of from 50° C. to 100° C. and, preferably at a temperature of from 70° C. to 90° C.

EP 2441751 A1 discloses a method for preparing an alkyl sulfone compound using an oxidizing agent in the presence of a tungstate catalyst at a reaction temperature of 0° C. to 200° C., and more preferably at 10° C. to 150° C.

EP 1334956 B1 discloses a method for preparing a sulfone or sulfoxide compound, which comprises reacting a sulfide compound with hydrogen peroxide in the presence of a metal oxide catalyst.

None of these publications disclose a catalytic oxidation for preparing fluensulfone as disclosed in the present invention.

SUMMARY OF THE INVENTION

The present invention provides a process for preparing a compound of formula (I)

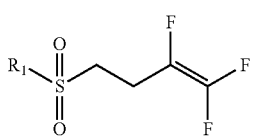

wherein $R_1$ is optionally substituted heterocyclic aromatic ring,
which comprises reacting a compound of formula (II)

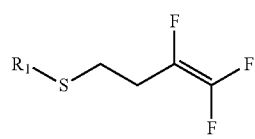

with an oxidizing agent and a catalyst at a low temperature.

The present invention also provides a method of increasing the yield of a compound of formula (I) in a process of oxidation of a compound of formula (II), which involves reacting a compound of formula (II) with an oxidizing agent and a catalyst at a low temperature.

The present invention also provides a method of increasing the selectivity of a compound of formula (I) in a process of oxidation of a compound of formula (II), which involves reacting a compound of formula (II) with an oxidizing agent and a catalyst at a low temperature.

DETAILED DESCRIPTION OF THE INVENTION

Definitions

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains. The following definitions are provided for clarity.

The term "a" or "an" as used herein includes the singular and the plural, unless specifically stated otherwise. Therefore, the terms "a," "an," or "at least one" can be used interchangeably in this application.

As used herein, the term "about" when used in connection with a numerical value includes ±10% from the indicated value. In addition, all ranges directed to the same component or property herein are inclusive of the endpoints, are independently combinable, and include all intermediate points and ranges. It is understood that where a parameter range is provided, all integers within that range, and tenths thereof, are also provided by the invention.

As used herein, the term "efficient" when used refers to reaction time of less than 24 hours.

As used herein, the term "mixture" or "combination" refers, but is not limited to, a combination in any physical form, e.g., blend, solution, alloy, or the like.

The term "heterocyclic aromatic ring" refers to thiophene, thiazole and thiadiazole.

The term "optionally substituted" refers to H and halogen.

The present invention is based on the inventors' surprising finding that the catalytic oxidation of the compound 5-chloro-2-[(3,4,4-trifluoro-3-buten-1-yl)thio]-thiazole to synthesize the compound fluensulfone at a low temperature, provides an efficient process with high selectivity, conversion and yield.

The present invention is advantageous in that it is highly efficient. In particular, the processes disclosed herein provides a highly selective reaction exhibiting a high conversion rate, higher yields, reduced cost of production and simplified work-up. The present invention is also advantageous in that it is atom efficient and it minimizes the amount of generated salt wastes.

In the oxidation process of a sulfide to the corresponding sulfone, represented by Scheme 1, the intermediate sulfoxide (II') is formed readily, however, the second oxidation to the sulfone is commonly slower, and requires elevated temperatures.

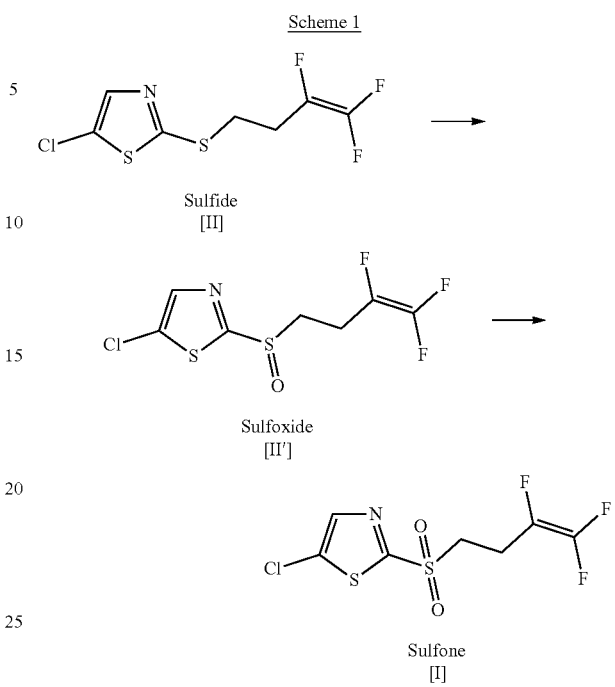

Such oxidation processes, generally lead to the undesired oxidation of the double bond of the highly reactive halogenated butenyl group of fluensulfone and to its oxidative degradation, leading to low selectivity of the reaction and as a consequence to low yields.

Scheme 2 represents some examples of such an oxidative degradation and the subsequent formation of a by-products.

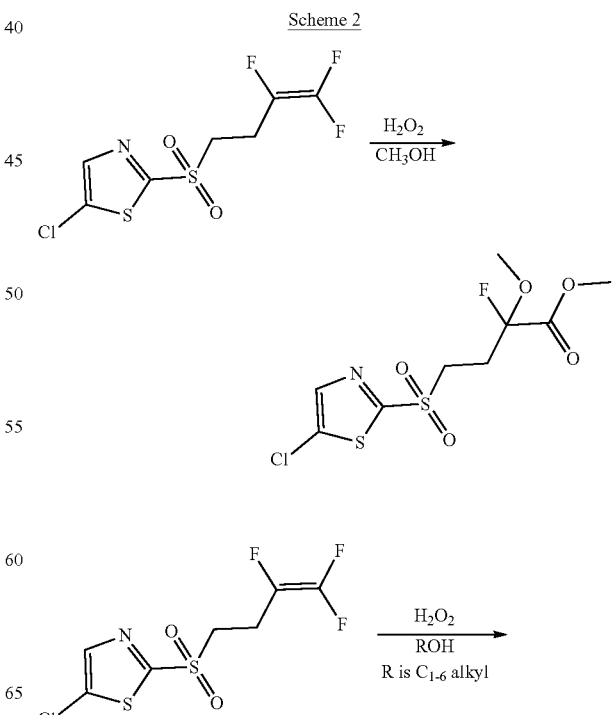

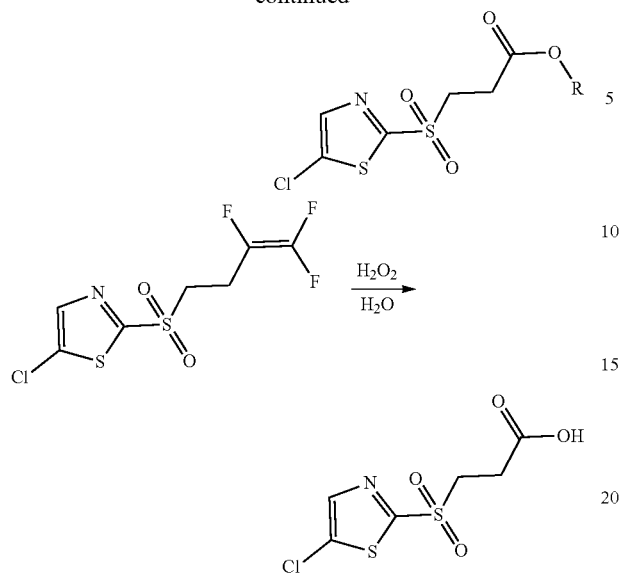

Figure 1:
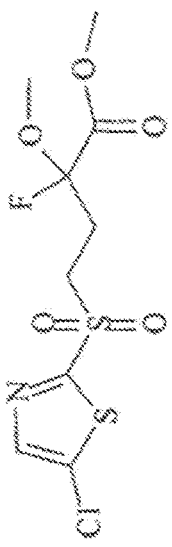
FIG. 1 shows the mass spectrograms of by-products produced by oxidative degradation as depicted in Scheme 2.
Figure 1:
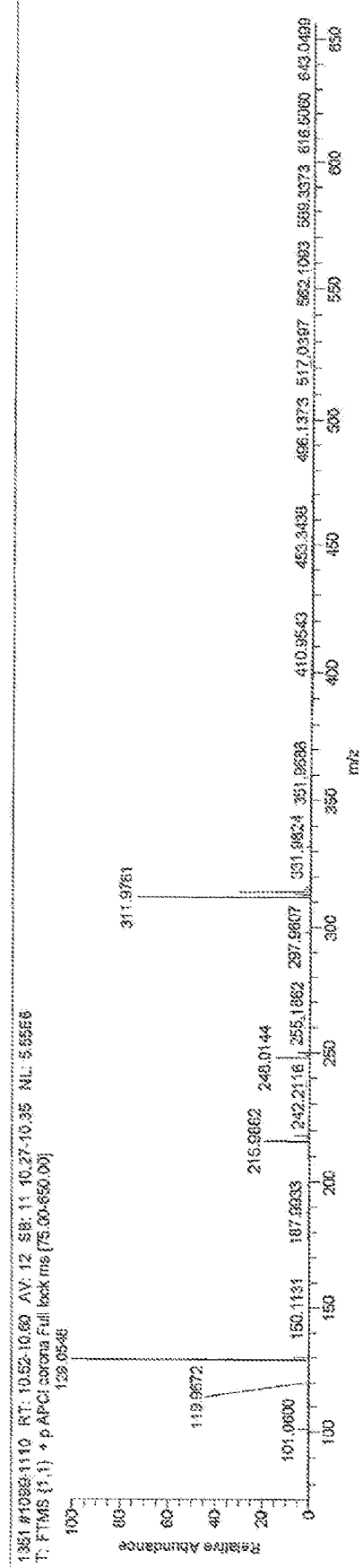
Figure 2:
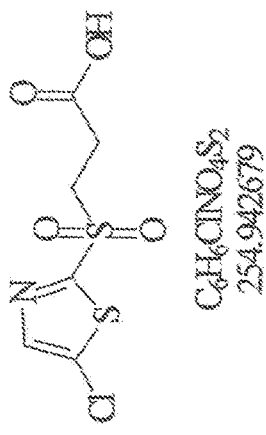
FIG. 2 shows the mass spectrograms of by-products produced by oxidative degradation as depicted in Scheme 2.
Figure 2:
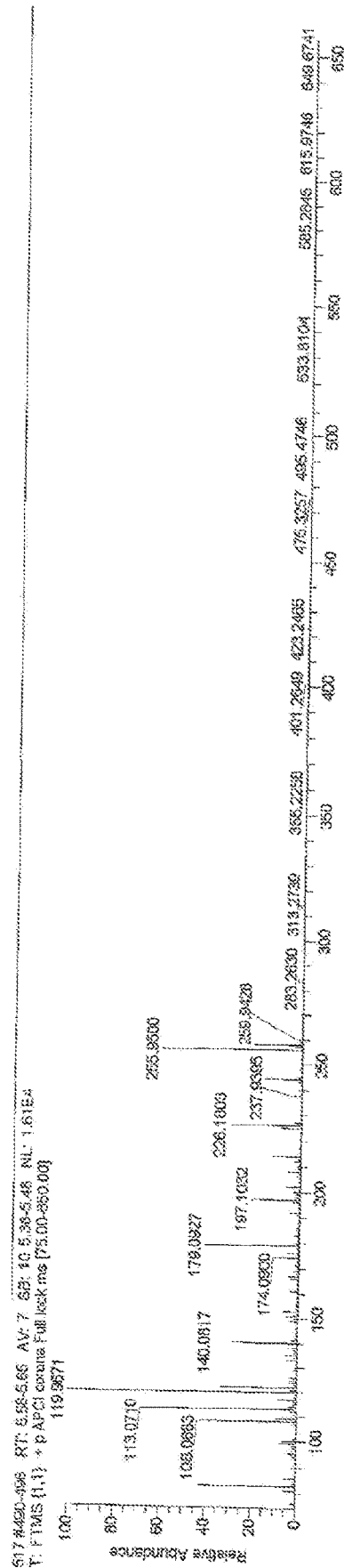
Figure 3:
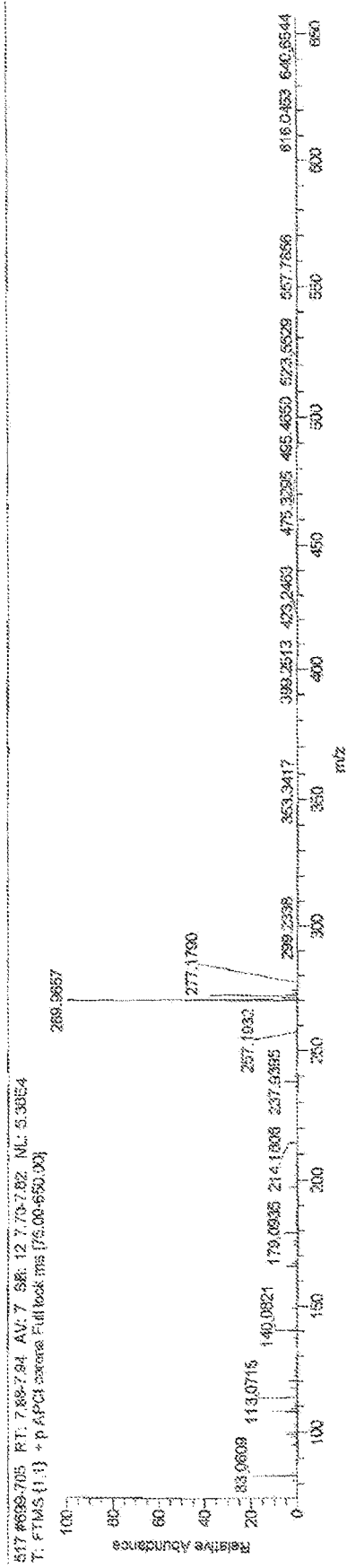
FIG. 3 shows the mass spectrograms of by-products produced by oxidative degradation as depicted in Scheme 2.

The impurities were identified by MS as shown in FIGS. 1-3.

In view of the oxidation susceptible double bond of the compound of formula [I], it was an object of the present invention to provide a process for preparing a sulfone of formula [I] by oxidation of the corresponding sulfide, obtaining high selectivity, conversions and yields, while minimizing the amount of wastes.

The inventors found that the catalytic oxidation of a compound of formula [II] at low temperatures, provides high selectivity up to high conversions and therefore high yield of the corresponding sulfone.

The present invention provides a process for preparing a compound of formula [I], the process comprises reacting the compound of formula [II] with an oxidizing agent and a catalyst, at low temperature.

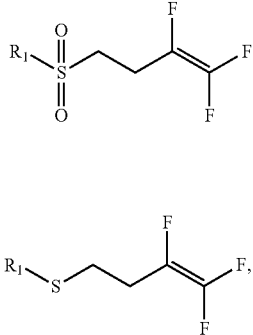

wherein, $R_1$ is optionally substituted heterocyclic aromatic ring.

The present invention provides a process for preparing a compound of formula [I], the process comprises reacting the compound of formula [II] with an oxidizing agent and a catalyst, wherein the process is carried out at a temperature of about −5° C.-25° C.

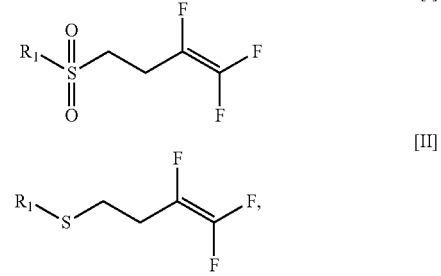

wherein, $R_1$ is optionally substituted heterocyclic aromatic ring.

The present invention provides a process for preparing a compound of formula [I], the process comprises reacting the compound of formula [II] with an oxidizing agent and a catalyst, wherein the process is carried out at a temperature of about −5° C.-25° C. In some embodiments, the temperature is between 0° C.-20° C. In some embodiments, the temperature is between 5° C.-15° C. In a preferred embodiment, the temperature is between 8° C.-10° C.

Oxidizing agents used for the catalytic oxidation can be agents usually used for this purpose in organic chemistry and which are known to a person skilled in the art including for example hydrogen peroxide, m-chloroperoxybenzoic acid, peroxyacetic acid, peroxy-benzoic acid, magnesium monoperoxyphthalate, potassium peroxymonosulfate, bis(trimethylsilyl) peroxide, methylsilyl peroxide, nickel peroxide, trifluoroperacetic acid, 2,4-dinitroperbenzoic acids, peroxysulfuric acid, carbonoperoxoic acid, sodium perborate monohydrate, tertbutyl hydroperoxide (TBHP), etc.

In some embodiments, the oxidizing agent is peroxide.

In some embodiments, the oxidizing agent is hydrogen peroxide.

In some embodiments, the concentration of hydrogen peroxide in water is at least 10%, 20%, 30%, 40% or 50%.

In some embodiments, the concentration of hydrogen peroxide in water is at least 30%. In a preferred embodiment, the concentration of hydrogen peroxide in water is 50%.

In some embodiments, the oxidizing agent is used as a solution.

In some embodiments, the catalyst may include but are not limited to $TaCl_5$, $Ta(OEt)_5$, $NbCl_5$, $Nb_2O_5$, $TiO_2/H_3PO_4$, $Ti(OiPr)_4$, $V_2O_3$, $V_2O_5$, $VO(aCaC)_2$, $Na_2WO_4$, $WO_2$, $WO_3$, WO, $WF_6$, wrought tungsten and two tungsten-copper pseudoalloys, W metal, W metal in combination with $Al_2O_3$, $WF_6$, mixed oxo-flurocomplexes of W(VI), $WO_5 \cdot HMPT \cdot H_2O$ (HMPT=hexamethyl phosophoric acid triamide), mixed oxo-flurocomplexes of W(IV), $WO_2F_2$, $WOF_4$, mixed oxo-chlorocomplexes of W(IV): $WO_2Cl_2$, $WOCl_4$, $W(CO)_6$, $H_2WO_4$(aq.), $MoO_3$, $Na_2MoO_4$, $H_4PMo_{11}VO_{40}$, and combination thereof. In a preferred embodiment the catalyst is selected from niobium pentachloride, tantalum pentachloride, sodium tungstate, and sodium molybdate. In a most preferred embodiment, the catalyst is sodium tungstate.

In some embodiments, the process is carried out in a solvent.

Solvent includes, but is not limited to polar and non-polar solvents.

In some embodiments, the solvent is a polar solvent. In some embodiments, the solvent is a non-polar solvent. In some embodiment, the solvent is a mixture of at least one polar solvent and at least one non-polar solvent.

Polar solvents may include but are not limited to nitriles, alcohols, ethers, chlorinated solvents, and combination thereof.

In some embodiments, the polar solvent is an alcohol solvent. In some embodiments, the alcohol solvent is a $C_{1-6}$ alcohols. In some embodiments, the alcohol solvent is methanol. In some embodiments, the alcohol solvent is ethanol. In some embodiments, the alcohol solvent is isopropanol. In some embodiments, the alcohol solvent is butanol. In some embodiments, the alcohol solvent is pentanol. In some embodiments, the alcohol solvent is hexanol. In some embodiments, the alcohol solvent is ethylene glycol.

In some embodiments, the alcohol solvent is methanol, ethanol, isopropanol, butanol, pentanol, hexanol, ethylene glycol or a combination thereof.

In some embodiments, the polar solvent is a nitrile solvent. In some embodiments, the nitrile solvent is a $C_1$-$C_6$ nitrile. In some embodiments, the nitrile solvents may include but are not limited to acetonitrile, isobutyronitrile, propionitrile, acrylonitrile or a combination thereof. In some embodiments, the nitrile solvent is acetonitrile.

Non polar solvents may include but are not limited to optionally substituted aliphatic, alicyclic and aromatic solvents such as hexane, cyclohexane, petroleum, ether, ligroine, benzene, toluene, xylene, methylene chloride, chloroform, carbon tetrachloride, ethylene chloride, chlorobenzene, or a combination thereof.

In some embodiments, the non-polar solvent is an aromatic non-polar solvent. In some embodiments, the aromatic non-polar solvent is toluene.

In some embodiments, the non-polar solvent is an aliphatic hydrocarbon non-polar solvent.

In some embodiments, the aliphatic hydrocarbon non-polar solvent is hexane.

In some embodiments, the polar or non-polar solvent is a chlorinated solvent. In some embodiments, the chlorinated solvents may include but are not limited to methylene chloride, chloroform, carbon tetrachloride, ethylene chloride and chlorobenzene.

In some embodiments, the process is carried out in a solvent selected from methanol, acetonitrile, and toluene or a combination thereof. In a preferred embodiment, the solvent is methanol.

In some embodiments, the molar ratio between the compound of formula [II] and the catalyst is from 1:1 to 100:1. In some embodiments, the molar ratio between the compound of formula [II] and the catalyst is from 10:1 to 20:1. In some embodiments, the molar ratio between the compound of formula [II] and the catalyst is about 15:1.

In some embodiments, the molar ratio between the compound 5-chloro-2-[(3,4,4-trifluoro-3-buten-1-yl)thio]-thiazole and the catalyst is from 1:1 to 100:1. In some embodiments, the molar ratio between the compound 5-chloro-2-[(3,4,4-trifluoro-3-buten-1-yl)thio]-thiazole and the catalyst is from 10:1 to 20:1. In some embodiments, the molar ratio between the compound 5-chloro-2-[(3,4,4-trifluoro-3-buten-1-yl)thio]-thiazole and the catalyst is about 15:1.

In some embodiments, the molar ratio between the compound of formula [II] and the oxidizing agent is from 1:1 to 1:10. In some embodiments, the molar ratio between the compound of formula [II] and the oxidizing agent is from 1:1 to 1:5. In a preferred embodiment, the molar ratio between the compound of formula [II] and the oxidizing agent is about 1:4.

In some embodiments, the molar ratio between the compound 5-chloro-2-[(3,4,4-trifluoro-3-buten-1-yl)thio]-thiazole and the oxidizing agent is from 1:1 to 1:10. In some embodiments, the molar ratio between the compound 5-chloro-2-[(3,4,4-trifluoro-3-buten-1-yl)thio]-thiazole and the oxidizing agent is from 1:1 to 1:5. In a preferred embodiment, the molar ratio between the compound 5-chloro-2-[(3,4,4-trifluoro-3-buten-1-yl)thio]-thiazole and the oxidizing agent is about 1:4.

In some embodiments, the molar ratio between the oxidizing agent and the catalyst is between 1000:1 to 10:1. In some embodiments, the molar ratio between the oxidizing agent and the catalyst is between 100:1 to 20:1. In some embodiments, the molar ratio between the oxidizing agent and the catalyst is 60:1.

In some embodiments, the process is carried out for less than 24 h, 22 h, 20 h, 18 h, 16 h, 12 h, 10 h, 8 h, 6 h, or 4 h.

In some embodiments, the conversion of the compound of formula [II] to the compound of formula [I] is higher than 90%, 95%, 99%, or 100%.

In some embodiments, the conversion of 5-chloro-2-[(3,4,4-trifluoro-3-buten-1-yl)thio]-thiazole to fluensulfone is higher than 90%, 95%, 99%, or 100%.

In some embodiments, the chemical yield of the compound of formula [I] is higher than 80%, 85%, 90%, or 95%.

In some embodiments, the chemical yield of the fluensulfone is higher than 80%, 85%, 90%, or 95%.

Phase separation and crystallization with methyl cyclohexane or n-heptane provides an excellent purification from the impurities.

Phase separation and crystallization with methyl cyclohexane or n-heptane provides an excellent purification of fluensulfone from the impurities.

The recrystallization is carried out by cooling a hot saturated solution of a non-polar solvent such as methyl cyclohexane or heptane or a combination thereof, at a temperature range of about 0-70° C.

Compound of formula [I] is obtained in a yield higher than 80%, 85%, 90%, or 95%. The yield of the purified sulfone product is higher than 80%.

Fluensulfone is obtained in a yield higher than 80%.

The present invention also provides a method of increasing the yield of a compound of formula (I) in a process of oxidation of a compound of formula (II), which involves reacting a compound of formula (II) with an oxidizing agent and a catalyst at a low temperature. In some embodiments the compound of formula (I) is fluensulfone.

The present invention also provides a method of increasing the selectivity of a compound of formula (I) in a process of oxidation of a compound of formula (II), which involves reacting a compound of formula (II) with an oxidizing agent and a catalyst at a low temperature. In some embodiments the compound of formula (I) is fluensulfone.

The present invention also provides a method of increasing the yield of a compound of formula (I) in a process of oxidation of a compound of formula (II), which involves reacting a compound of formula (II) with an oxidizing agent and a catalyst at a temperature of about −5° C.-25° C. In some embodiments the compound of formula (I) is fluensulfone.

The present invention also provides a method of increasing the selectivity of a compound of formula (I) in a process of oxidation of a compound of formula (II), which involves reacting a compound of formula (II) with an oxidizing agent and a catalyst at a temperature of about −5° C.-25° C. In some embodiments the compound of formula (I) is fluensulfone.

In some embodiments, the temperature is between 0° C.-20° C. In some embodiments, the temperature is between 5° C.-15° C. In a preferred embodiment, the temperature is between 8° C.-10° C.

The present invention also provides an improved process for obtaining a compound of formula (I), which involves reacting a compound of formula (II) with an oxidizing agent and a catalyst at a low temperature.

The present invention also provides an improved process for obtaining a compound of formula (I), which involves reacting a compound of formula (II) with an oxidizing agent and a catalyst at a temperature of about −5° C.-25° C.

In some embodiments, the temperature is between 0° C.-20° C. In some embodiments, the temperature is between 5° C.-15° C. In a preferred embodiment, the temperature is between 8° C.-10° C.

In some embodiments, the improvement comprises obtaining at least 90%, or 95%, or 99%, or 100% conversion of the compound of formula (II) to the compound of formula (I). In some embodiments, the improvement comprises obtaining a conversion of more than 90%, or 95%, or 99%, or 100% of the compound of formula (II) to the compound of formula (I). In some embodiments the compound of formula (I) is fluensulfone.

In some embodiments, the improvement comprises obtaining at least 80%, 85%, 90%, or 95% chemical yield of the compound of formula (I). In some embodiments the compound of formula (I) is fluensulfone.

EXPERIMENTAL SECTION

Example 1

20.0 g of 5-chloro-2-[(3,4,4-trifluoro-3-buten-1-yl)thio]-thiazole (96.8%, 74.55 mmol) and 100 g methanol were added to a 1 L flask equipped with mechanical stirrer, condenser, thermometer and dropping funnel. A solution of 1.7 g Na$_2$WO$_4$*2H$_2$O (5.10 mmol) in 14 mL water were added to the reaction mixture, and the reaction mixture was cooled to 10° C.

21.0 g H$_2$O$_2$ (50% in water, 17.5 mL, 308.73 mmol) were added slowly over 6 h while the reaction was stirred at 8–10° C. After full addition of H$_2$O$_2$ the reaction was stirred at 8–10° C. for another 1 to 4 h. Samples were taken to analysis (LC) at the end of the feeding and periodically until the sulfoxide (formula II') is <1% by normalization.

After the reaction was completed, the reaction mixture was cooled to 5° C., and Na$_2$S$_2$O$_5$ was added slowly until the peroxide test was negative, keeping the temperature between 5-20° C. The methanol was removed by vacuum distillation and 40 mL of water was added.

The pH was slowly corrected to 6-7 using 15% NaOH solution and the reaction mixture was stirred for another 15 minutes.

120 g Methyl cyclohexane were added and heated to 70° C. and the phases were separated hot. The organic phase was washed with 100 g water at 70° C., and the phases were separated hot.

A gradual crystallization from 70° C. to 0° C. was performed and the reaction mixture was filtered at 0° C. The cake was dried on the sinter and later in vacuum (10 mbar at 25° C.).

After drying 85-91% yield of fluensulfone was obtained (assay higher than 97%).

DISCUSSION

Oxidation of sulfide in the presence of an alkene group is challenging, increasing the selectivity effects the yield and the efficiency. It was found that a catalytic oxidation at low temperature is efficient and provides high selectivity.

What is claimed:

1. A process for preparing a compound of formula [I], the process comprises:
    (a) reacting a compound of formula [II] with an oxidizing agent and a catalyst, wherein the process is carried out at a temperature of about −5° C.-25° C.

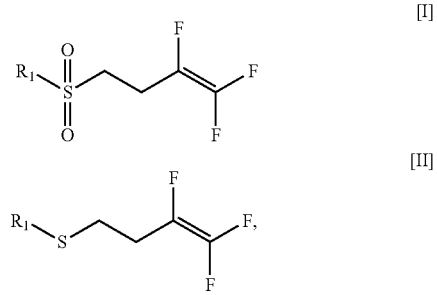

wherein, R$_1$ is an optionally substituted heterocyclic aromatic ring, wherein the catalyst is selected from the group consisting of TaCl$_5$, Ta(OEt)$_5$, NbCl$_5$, Nb$_2$O$_5$, TiO$_2$/H$_3$PO$_4$, Ti(OiPr)$_4$, V$_2$O$_3$, V$_2$O$_5$, VO(acac)$_2$, Na$_2$WO$_4$, WO$_2$, WO$_3$, WO, WF$_6$, wrought tungsten and two tungsten-copper pseudoalloys, W metal, W metal in combination with Al$_2$O$_3$, WF$_6$, mixed oxo-flurocomplexes of W(VI), WO$_5$·HMPT·H$_2$O wherein HMPT is hexamethyl phosophoric acid triamide, mixed oxo-flurocomplexes of W(IV), WO$_2$F$_2$, WOF$_4$, mixed oxo-chlorocomplexes of W(IV), WO$_2$Cl$_2$, WOCl$_4$, W(CO)6, H$_2$WO$_4$(aq,), MoO$_3$, Na$_2$MoO$_4$, and H$_4$PMo$_{11}$VO$_{40}$; and
    (b) obtaining the compound of formula (I).

2. The process according to claim 1, wherein the temperature is about 0° C. -20° C.

3. The process according to claim 1, wherein the temperature is about 5° C. -15° C.

4. The process according to claim 1, wherein the temperature is about 8° C. -10° C.

5. The process according to claim 1, wherein the oxidizing agent is selected from a group consisting of hydrogen peroxide, m-chloroperoxybenzoic acid, peroxyacetic acid, peroxy-benzoic acid, magnesium monoperoxyphthalate, potassium peroxymonosulfate, bis(trimethylsilyl) peroxide, methylsilyl peroxide, nickel peroxide, trifluoroperacetic acid, 2,4-dinitroperbenzoic acids, peroxysulfuric acid, carbonoperoxoic acid, sodium perborate monohydrate, and tertbutyl hydroperoxide.

6. The process according to claim 5, wherein the oxidizing agent is hydrogen peroxide.

7. The process according to claim 6, wherein the concentration of hydrogen peroxide in water is at least 30%.

8. The process according to claim 7, wherein the concentration of hydrogen peroxide in water is 50%.

9. The process according to claim 1, wherein the catalyst is selected from the group consisting of TaCl$_5$, Ta(OEt)$_5$, NbCl$_5$, Nb$_2$O$_5$, TiO$_2$/H$_3$PO$_4$, Ti(OiPr)$_4$, V$_2$O$_3$, V$_2$O$_5$, VO(acac)$_2$, Na$_2$WO$_4$, WO$_2$, MoO$_3$, Na$_2$MoO$_4$, and H$_4$PMo$_{11}$VO$_{40}$.

10. The process according to claim 9, wherein the catalyst is selected from the group consisting of NbCl$_5$, TaCl$_5$, Na$_2$WO$_4$ and Na$_2$MoO$_4$.

11. The process according to claim 10, wherein the catalyst is Na$_2$WO$_4$.

12. The process according to claim 1, wherein the process is carried out in a solvent selected from a group consisting of alcohols, nitriles, ethers, chlorinated solvents, optionally substituted aliphatic, alicyclic and aromatic solvents or a combination thereof.

13. The process according to claim 12, wherein the process is carried out in a solvent selected from a group consisting of methanol, acetonitrile, toluene or a combination thereof.

14. The process according to claim 12, wherein the solvent is methanol.

15. The process according to claim 1, wherein the molar ratio between the compound of formula [II] and the catalyst is from 1:1 to 100:1.

16. The process according to claim 15, wherein the molar ratio between the compound of formula [II] and the catalyst is from 10:1 to 20:1.

17. The process according to claim 15, wherein the molar ratio between the compound of formula [II] and the catalyst is 15:1.

18. The process according to claim 1, wherein the molar ratio between the compound of formula [II] and the oxidizing agent is from 1:1 to 1:10.

19. The process according to claim 18, wherein the molar ratio between the compound of formula [II] and the oxidizing agent is from 1:1 to 1:5.

20. The process according to claim 18, wherein the molar ratio between the compound of formula [II] and the oxidizing agent is about 1:4.

21. The process according to claim 1, wherein the process is carried out for less than 24h.

22. The process according to claim 21, wherein the process is carried out for less than 12h.

23. The process according to claim 22, wherein the process is carried out for less than 10h.

24. The process according to claim 1, wherein the conversion of a compound of formula [II] to a compound of formula [I] is higher than 90%.

25. The process according to claim 1, wherein the chemical yield is higher than 85%.

26. The process according to claim 1, wherein the compound of formula [I] is further purified by recrystallization.

27. The process according to claim 26, wherein the recrystallization is by cooling a hot saturated solution.

28. The process according to claim 26, wherein the recrystallization is by cooling a hot saturated solution of a non-polar solvent.

29. The process according to claim 28, wherein the non-polar solvent is methyl cyclohexane or heptane or a combination thereof.

30. The process according to claim 26, wherein the purification is carried out at a temperature range of about 0-70° C.

31. The process according to claim 26, wherein the yield of the purified product is higher than 80%.

32. The process according to claim 1, wherein $R_1$ is selected from a group consisting of optionally substituted thiophene, optionally substituted thiazole and optionally substituted thiadiazole.

33. The process according to claim 1, wherein the compound of formula [I] is fluensulfone.

34. The process according to claim 1, wherein the compound of formula [II] is chloro-2-[(3,4,4-trifluoro-3-buten-1-yl)thio]-thiazole.

* * * * *